(12) United States Patent
Hobby et al.

(10) Patent No.: US 7,102,346 B2
(45) Date of Patent: Sep. 5, 2006

(54) MEASURING CELL FOR DETERMINING CHARACTERISTICS OF A PARAMAGNETIC GAS BASED ON GAS FLOW SWEEPING PAST A TEST ELEMENT

(75) Inventors: James Hobby, Crowborough (GB); Danny Holman, Crowborough (GB)

(73) Assignee: Servomex Group Ltd., East Sussex (GB)

(*) Notice: Subject to any disclaimer, the term of this patent is extended or adjusted under 35 U.S.C. 154(b) by 66 days.

(21) Appl. No.: 10/485,702

(22) PCT Filed: Aug. 2, 2002

(86) PCT No.: PCT/GB02/03558

§ 371 (c)(1),
(2), (4) Date: Aug. 9, 2004

(87) PCT Pub. No.: WO03/012424

PCT Pub. Date: Feb. 13, 2003

(65) Prior Publication Data

US 2004/0255642 A1    Dec. 23, 2004

(30) Foreign Application Priority Data

Aug. 2, 2001    (GB) ................... 0118937.2

(51) Int. Cl.
*G01N 27/74* (2006.01)
*G01R 33/12* (2006.01)

(52) U.S. Cl. .................. 324/204; 73/25.02; 324/201

(58) Field of Classification Search ............. 324/204, 324/201; 73/25.02
See application file for complete search history.

(56) References Cited

U.S. PATENT DOCUMENTS

| 2,666,893 A | | 1/1954 | Munday |
|---|---|---|---|
| 4,807,463 A | * | 2/1989 | Ostermeier ............... 73/23.2 |
| 4,983,913 A | * | 1/1991 | Krause et al. ............. 324/204 |

FOREIGN PATENT DOCUMENTS

| EP | 0 379 553 B1 | 6/1989 |
|---|---|---|
| EP | 0 608 122 A2 | 1/1994 |
| EP | 0 926 490 A2 | 12/1998 |
| GB | 2 196 127 A | 10/1987 |
| WO | WO 89/12821 | 12/1989 |

OTHER PUBLICATIONS

International Search Report for PCT/GB02/03558 dated Dec. 12, 2002.

* cited by examiner

*Primary Examiner*—Jay M. Patidar
(74) *Attorney, Agent, or Firm*—Daly, Crowley, Mofford & Durkee, LLP

(57) ABSTRACT

A measuring cell for use in apparatus for the measurement of the magnetic characteristics of a gas comprises means (5) defining a chamber (3) in which a test element (11) is suspended such as to be able to rotate about an axis, and means de inlet (1) and outlet port (4) means by which gas may flow through said chamber (3). The inlet port means is configured to cause the gas to flow in a substantially laminar flow regime. The chamber comprises a first portion (2) configured to cause the laminar gas flow to break up into a turbulent flow regime, and a second portion arranged to contain said test element. The gas flow enters from the first portion and enters the chamber in a flow pattern symmetrical in relation to the suspension position of the test element.

11 Claims, 1 Drawing Sheet

MEASURING CELL FOR DETERMINING CHARACTERISTICS OF A PARAMAGNETIC GAS BASED ON GAS FLOW SWEEPING PAST A TEST ELEMENT

CROSS-REFERENCE TO RELATED APPLICATIONS

This application is a National Stage application of PCT Application No. PCT/GB02/03558, filed Aug. 2,2002 and claims the of GB Application No. 0118937.2, filed on Aug. 2, 2001, both of which are incorporated herein by reference.

1. FIELD OF THE INVENTION

The present invention relates to apparatus for the measurement of gases. In particular it relates to the control of a gaseous sample, e.g oxygen, for introduction into a measuring system when rapid changes in the make-up of the sample are occurring.

2. DESCRIPTION OF THE PRIOR ART

Within gas sensing one of the most difficult applications is the introduction of the gas sample into apparatus used to measure the susceptibility of a gas. Apparatus for controlling the sample introduced to such a gas sensor come in a variety of forms. The measurement of the proportion of oxygen in a sample using susceptibility has been known since the middle of the $19^{th}$ century when Faraday showed that all materials interacted with a magnetic field. Gases were found in general to be repelled by a magnetic field and are described as being diamagnetic, whilst oxygen and some other gases were found to be attracted to a magnetic field and called paramagnetic.

Two principal methods were originally developed, Gouy (Gouy L G, Compt. Rend. Vol. 109 (1889) 935) employed a uniform magnetic field whilst Selwood (Selwood P W Magnetometry 2nd Edition, 193. Interscience N/Y London 1956) used the non-uniform field as originally described by Faraday. The bulky and delicate nature of these instruments led to the development of further apparatus amongst which the most successful were those based on the original Faraday gas susceptibility balance. In these designs a test body of well defined shape is suspended inside a gas cell. Several forms of test body have been investigated including the commonly used dumbbell by Haven (Haven GC Physical Review Vol. 4 (1932) 337) with modifications using a flattened structure eg. by Gast in U.S. Pat. No. 3,815,018.

Although these methods can provide a highly accurate signal under ideal gas conditions (i.e. with no gas movement) the existence of gas flow introduces errors due the extra forces created by the passage of the sample. For many applications the relatively slow response times desired, for example three to five seconds, allows a diffusion based sample system which minimises gas flows to be employed. However, some applications, notably pulmonary testing and breath by breath anaesthetic monitoring, have required response times in the sub second range. It has therefore been necessary for methods of sample introduction to be developed that introduce the sample into the measurement chamber such that the delays encountered by a purely diffusive nixing are not met. An example of this is given in EP 0379553, which describes a combination of small cell volume and sample flow regime than can produce responses times of approximately 0.5 s at a flow rate of 50 ml/min.

GB-A-2196127 discloses an alternative paramagnetic sensor design which the gas path is arranged to have smooth transistions of constant cross section, or gently tapering or widening transitions, between various regions in order to produce a smooth unobstructed gas flow. This in intended to achieve an undisrupted, non-turbulent gas flow.

The devices in the prior art do not meet all of the requirements now desired and in particular have limitations in the sample cell size that may be employed or flow errors that have to be tolerated in order to achieve the necessary speed of response.

SUMMARY OF THE INVENTION

The present invention provides apparatus for the measurement of the magnetic characteristics of a gas comprising means defining a chamber, a test element, means for suspending said test element in said chamber such that said test element may rotate about an axis and means defining inlet and outlet port means by which gas may flow through said chamber, wherein said inlet port means is configured to receive an inflow of gas, and to cause said gas to flow in a substantially laminar flow regime and said chamber comprises a first portion which said gas flow enters from said inlet port and which is configured to cause said laminar gas flow to break up into a turbulent flow regime, and a second portion containing said test element which said gas flow enters from said first portion and which is configured such that the gas flow principally sweeps past said element to reach said outlet port means.

The present invention therefore functions to control the flow of gas so as to reduce components of the flow which would move the measuring device so as to cause errors in the measurement. This arrangement minimises the errors, but provides a quick response time as it relies on flow to introduce the sample of the measuring chamber rather than diffusion.

The invention also provides apparatus for the measurement of characteristics of a gas comprising means defining (i) a pair of inlet means arranged to receive a flow of said gas and to cause laminar flow of said gas therein, (ii) a respective pair of expansion volumes each being arranged in relation to a respective one of said inlet means to receive said gas flow therefrom and to cause said gas flow to expand in directions normal to the direction of said laminar flow to become a turbulent flow, (iii) a measurement volume arranged to receive said flow from said pair of expansion volumes, and (iv) outlet means arranged to exhaust gas from said measurement volume, said apparatus further comprising means arranged to suspend a test element in said measurement volume substantially symetrically in relation to said expansion volumes.

This invention therefore, in contrast to the prior art which generally avoided causing turbulent flows on the basis that such flows would introduce errors, causes and utilises turbulent flow in the gas path, while still reducing the errors introduced into the system.

BRIEF DESCRIPTION OF THE DRAWINGS

This invention will be better understood from the following exemplary description of a preferred embodiment given with reference to the accompanying drawings in which.

DETAILED DESCRIPTION OF THE DRAWINGS

The apparatus described herein allows for the measurement of a gas sample in a sensor which is perturbed by rapid changes in both flow rate and gas composition, e.g. the measurement of gas susceptibility using a test body suspended within a non-uniform magnetic field, where it is desired to minimise the effects of the gas flow. The principles of the measurement techniques are well known in the prior art above and will not be discussed here. The important features of the new apparatus lie in how the sample is introduced into the measurement cell that contains the test body, and in the shaping of the flow paths to achieve this.

Figure 1:
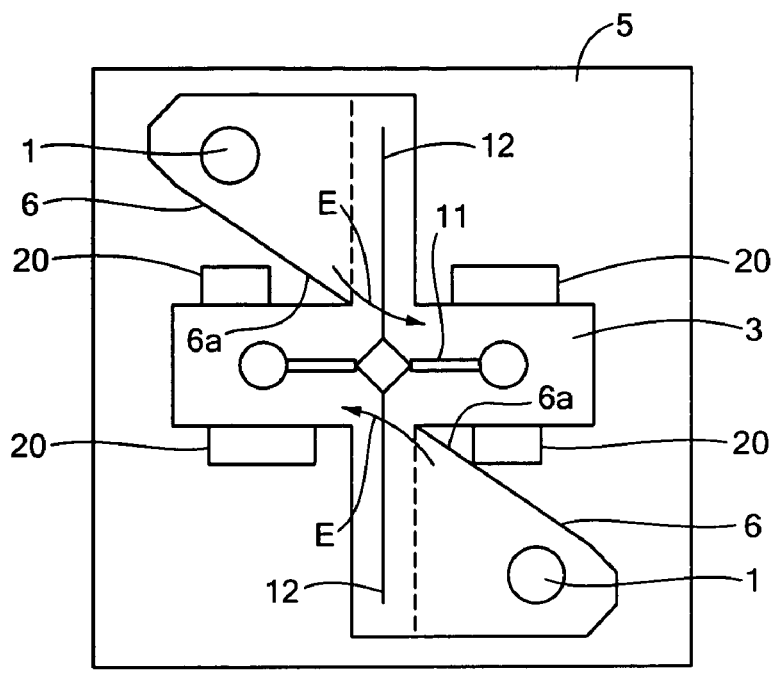
FIG. 1 is a schematic front view of the preferred device.

FIG. 1 is a schematic front view illustrating the preferred embodiment. In particular FIG. 1 shows a body 5 having within it various flow pathways and a measuring chamber as will be discussed in detail below. In this embodiment, there is also a face plate, which is not shown in FIG. 1, but which closes the front of the measuring chamber. This is merely one example of the how the testing apparatus may be manufactured.

FIG. 1 then shows a measuring chamber 3 defined within body 5 having located therein a dumbell type test element 11 suspended by suspension elements 12. Dumbell 11 is suspended such that it may rotate about an axis defined by suspension element 12 which also function to permit an electric current to be passed to the test element 11. Body 5 further includes, or has associated with it, magnets, for instance as shown schematically by magnetic portions 20, arranged to generate a magnetic field within the measurement chamber.

As is well known the deflection or movement of the test element 11 about axis 12 within the magnetic field when current is applied is dependent on the magnetic susceptibility of the gas present in the chamber 3. Therefore, measurement of such movement gives a measure of that susceptibility. The particular methods of measurement are not described here as they do not form the subject matter of the present invention, but suitable methods may be found in the publications mentioned above and other patents assigned to Servomex.

It is sufficient to note however that, for accurate measurement, it should be ensured, as far as possible, that any movement of the test element 11 is a result of changes in the susceptibility of the gas present in the chamber, and/or the measurement method being used. Other factors causing movement of the test element may introduce errors into the measurements produced.

It is however, also desired that the sensor should be quickly sensitive to changes in a gas flow, and this requires efficient flushing of gas through the chamber. This raises the considerable risk of causing errors in the measurement mentioned above by the simple mechanical action of the gas flow moving the test element. i.e. blowing it out of position.

As can be seen in FIG. 1, the device further comprises two flow inlet ports 1 by which gas is introduced into the measuring chamber. The chamber within body 5 is shaped so as to control the amount of gas flow which impacts the test element such as to cause errors in the measurement mentioned above. There is also defined within body 5 an outlet or exhaust port which is not shown in FIG. 1.

Figure 2:
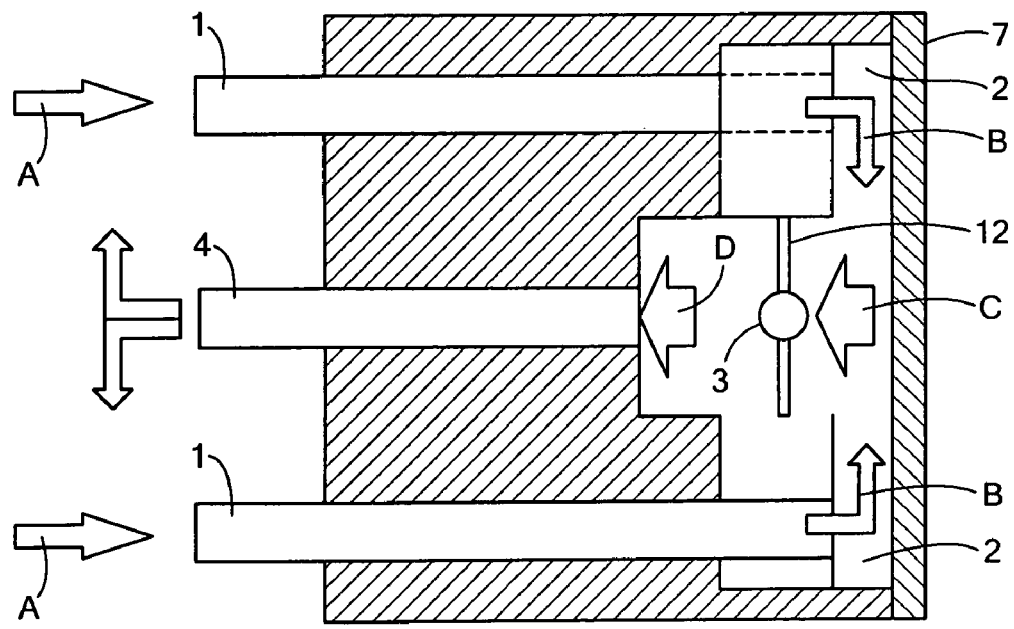
FIG. 2 is a schematic side sectional view of the device of FIG. 1.

FIG. 2 is a schematic side sectional view of the device shown in FIG. 1. FIG. 2 again shows the measurement chamber 3 having test element 11 suspended therein to rotate about the axis defined by suspension elements 12. Also as shown in FIG. 2, body 5 is provided with face plate 7 which completes the formation of the various flow paths to be discussed in detail below. Finally, the exhaust port 4 is shown in FIG. 2, but it should be noted that the features shown in FIGS. 1 and 2 are not drawn to scale.

Referring then to FIG. 2, the gas sample enters via ports 1 (arrows A). Inlet ports 1 are of a narrow diameter, for instance 1 mm to reduce any "smearing" of concentration changes in the gas flow., i.e. to ensure that such changes are efficiently passed into the device. At the front of the device, the gas flow is forced to undergo a ninety degree turn (arrows B) to enter a narrow channel 2 defined between body 5 and face plate 7. This turn breaks up the gas flow and causes the flow in channel 2 to have a wide distribution of momentum with no overall direct flow. The flow is at this stage made up of many very small vortices, and this can be considered analagous to creating a spray of fine water droplets at the outlet of a hosepipe by substantially obstructing the outlet.

The gas then enters the measuring chamber 3, where the large increase in cross section causes the flow per unit area to fall significantly. The test body 11 is mounted as shown such that it lies parallel to and in symmetrical relation to the narrow channel, 2. The gas then flows past the test element 11 (arrows C). The break up of the flow as mentioned above into many fine vortices is one factor which reduces the force the flow applies to the test element, because the forces of the vortices average out to be zero or near zero. Additionally, the differential force in a direction which would cause the test element to rotate created by the flow across the test body is negligible and therefore the measurement errors introduced by the flow or changes therein are further minimised.

Furthermore as the measurement chamber is actually being swept by the gas flow, rather than relying on diffusion, any change in sample concentration occurs rapidly. After passing through the measuring chamber the gas enters the exhaust port 4 (arrow D) accelerating the gas flow. However the port 4 is preferably larger than the inlet ports 1 (e.g. greater than 2 mm) to permit any chaotic flow to be rapidly expelled. Also, an extended gap at the back of the measuring chamber compared to the front reduces the effect of any turbulence generated as the sample enters the smaller bore outlet from acting on the test body and thereby re-introducing the flow errors the invention alleviates.

In FIG. 1 it can be seen that even further beneficial effects can be obtained within the present invention.

Here it can be seen that the narrow channel, mentioned above, has a gradually increasing width. This further decelerates the gas because of the increasing volume and brings the gas into contact with a large surface area thereby promoting the rapid removal of large scale turbulence in its flow straightening function. A further feature that is apparent in FIG. 1 is that the gas flow from either of the inlet ports 1 does not flow directly into the measuring chamber because of shielding portion 6. This shielding is one of the principal factors in determining the balance achieved between flow error and speed of response.

In the configuration shown in FIG. 1 the gas flow into the measuring chamber is as shown by arrow E. In this arrangement there is no or negligible gas momentum which impacts directly on the test element 11. Rather the gas simply sweeps past the test element. This is the most preferred arrangement from the viewpoint of measurement accuracy, and in fact, with this arrangement, the errors introduced by the gas flow are smaller than the error margin in many measurement methods, meaning that the gas flow errors are effectively zero.

If the amount of shielding at corners 6a is reduced which allows some of the sample to pass directly to the that portion of the measurement cell that lies nearest to it then the flow error will increase but will provide an improved response time. This trade off occurs because if the sample is allowed to flow significantly through the measurement chamber directly adjacent to an inlet port the flow will tend to flow asymmetrically around the test body. i.e. more flow passes between the nearer wall and the body than the further, producing an imbalanced force which leads directly to the flow error. Forcing the flow to pass through the centre point of the measurement chamber allows the sample to expand giving a more balanced flow either side of the test body.

Within this trade off it is possible to configure the test apparatus to be sensitive to changes of a few tenths of one percent oxygen level and with a response time less than 200 ms.

The above embodiment employs a torque balance type sensor to elucidate the function of the invention. However, the principle is applicable to wide range of devices which are susceptible to errors introduced by rapid changes in sample flow or composition and as such has a wider application than only to torque balance sensors.

Although the above description is of one preferred embodiment, it will be seen that there are important features of the embodiments which assist in achieving the object of the invention. These include the breaking up of the gas flow such that the gas flow around the test element has no relationship with the input gas flow. This enables the gas flows in the measurement chamber to be carefully controlled. The gas flows are controlled to have a low or zero velocity vector in the plane of sensitivity of the detector element, and the overall symmetry of the device assists here too.

What is claimed is:

1. Apparatus for measurement of the magnetic characteristics of a gas comprising:
    means (5) defining a chamber (3), having an inlet portion and a measuring portion in communication therewith;
    a test element (11);
    means for suspending said test element in said measuring portion of said chamber such that said test element may rotate about an axis (12); and
    means (5, 7) defining inlet and outlet port means by which gas may flow through said chamber (3), said inlet port means being provided in the inlet portion of the chamber and said outlet port means being provided in the measuring portion of the chamber;
    wherein said inlet port means is configured to receive an inflow of gas, and to cause said gas to flow in a substantially laminar flow regime into said inlet portion of said chamber which is configured to cause said laminar gas flow to break up into a turbulent flow regime, and wherein said measuring portion which contains said test element is configured to receive said turbulent gas flow from said inlet portion, said outlet port means being configured to receive said gas flow from said measuring portion, such that the gas flow principally sweeps past said element to reach said outlet port means.

2. Apparatus according to claim 1 in which said outlet port means has a cross-sectional area larger than that of said inlet port means.

3. Apparatus according to claim 1 in which said inlet port means comprises a pair of first inlet passageways, and said first portion of said chamber comprises a pair of respective expansion passageways in which said gas flows in said turbulent flow regions, said turbulent flow being substantially normal to the direction of flow in said inlet passageways.

4. Apparatus according to claim 3 in which the means defining the expansion passageways comprises a shielding portion (6) arranged to deflect the gas flow into the measuring portion of the chamber away from a direction parallel to said axis.

5. Apparatus according to claim 1 further comprising magnet means arranged to provide a magnetic field within said chamber.

6. Apparatus according to claim 1 in which said means for suspending said test elements enables the application of electric current to said element.

7. A measurement cell for use in apparatus for the measurement of the magnetic characteristics of a gas comprising;
    means (5) defining a chamber (3) in which a test element (11) is adapted to be suspended such as to be able to rotate about an axis; and
    means defining inlet and outlet port means by which gas is adapted to flow through said chamber (3);
    wherein said inlet port means is configured to receive an inflow of gas and to cause said gas to flow into the chamber in a substantially laminar flow regime; and said chamber comprises;
    a first portion (2) configured to receive said gas flow from said inlet port and which is configured to cause said laminar gas flow to break up into a turbulent flow regime; and
    a second portion arranged to contain said test element and which is configured to receive said turbulent gas flow from said first portion; said outlet port means being configured to receive the gas flow from said second portion;
    said first portion being arranged to cause the gas flow to enter said chamber in a flow pattern symmetrical in relation to the intended suspension position of said test element, and wherein the gas flow principally sweeps past said test element to reach said outlet port means.

8. A measurement cell according to claim 7 in which said outlet port means has a cross-sectional area larger than that of said inlet port means.

9. A measurement cell according to claim 7 in which said inlet port means comprises a pair of first inlet passageways, and said first portion of said chamber comprises a pair of respective expansion passageways in which said gas flows in said turbulent flow regime, said turbulent flow being substantially normal to the direction of flow in said inlet passageways.

10. A measurement cell according to claim 9 in which the means defining the expansion passageways comprises a shielding portion (6) arranged to deflect the gas flow into the second portion of the chamber away from a direction parallel to the direction of flow in said inlet passageways.

11. Apparatus for the measurement of characteristics of a gas comprising means defining (i) a pair of inlet means arranged to receive a flow of said gas and to cause laminar flow of said gas therein, (ii) a respective pair of expansion volumes each being arranged in relation to a respective one of said inlet means to receive said gas flow therefrom and to cause said gas flow to expand in directions normal to the direction of said laminar flow to become a turbulent flow, (iii) a measurement volume arranged to receive said turbulent flow from said pair of expansion volumes, and (iv) outlet means arranged to exhaust gas from said measurement volume, said apparatus further comprising means arranged to suspend a test element in said measurement volume substantially symetrically in relation to said expansion volumes.

* * * * *

UNITED STATES PATENT AND TRADEMARK OFFICE
CERTIFICATE OF CORRECTION

PATENT NO. : 7,102,346 B2
APPLICATION NO. : 10/485702
DATED : September 5, 2006
INVENTOR(S) : Hobby et al.

It is certified that error appears in the above-identified patent and that said Letters Patent is hereby corrected as shown below:

On the title page item (57) Abstract, line 5, delete "means de inlet" and replace with -- means defining inlet --.

Column 1, line 11, delete "claims the of GB" and replace with -- claims the benefit of GB --.

Column 1, line 49, delete "due the" and replace with -- due to the --.

Column 1, line 62, delete "responses" and replace with -- response --.

Column 3, line 26, delete "function" and replace with --functions --.

Column 4, line 34, delete "chamber the gas" and replace with -- chamber, the gas --.

Column 4, line 56, delete "FIG. 1 the gas" and replace with -- FIG. 1, the gas --.

Column 4, line 67, delete "directly to the that" and replace with --directly to the --.

Column 5, line 1, delete "to it then the flow" and replace with -- to it, then the flow --.

Column 5, line 5, delete "port the flow" and replace with -- port, the flow --.

Column 5, line 11, delete "flow either" and replace with -- flow to either --.

Column 5, line 17, delete "to wide range" and replace with -- to a wide range --.

Signed and Sealed this

Thirteenth Day of March, 2007

JON W. DUDAS
*Director of the United States Patent and Trademark Office*